United States Patent [19]

Isbell

[11] 4,338,465

[45] Jul. 6, 1982

[54] SYNTHESIZED SCENT

[75] Inventor: Arthur F. Isbell, Bryan, Tex.

[73] Assignee: Meiller Research, Inc., College Station, Tex.

[21] Appl. No.: 70,354

[22] Filed: Aug. 28, 1979

Related U.S. Application Data

[62] Division of Ser. No. 885,941, Mar. 13, 1978, Pat. No. 4,213,875.

[51] Int. Cl.³ .................... C07C 148/00; C07C 149/08

[52] U.S. Cl. ................................ 568/69; 252/188.3 R; 252/1

[58] Field of Search .................... 568/69; 252/188.3 R, 252/1

[56] References Cited

U.S. PATENT DOCUMENTS

| | | | |
|---|---|---|---|
| 3,093,666 | 6/1963 | DuBrow | 260/404.5 |
| 3,260,748 | 7/1966 | Nelson, Jr. | 568/67 X |
| 3,634,513 | 1/1972 | Fostor | 568/67 X |

OTHER PUBLICATIONS

D. F. Lee et al., Chemistry & Industry, Jul. 2, 1960, pp. 868–869.

Anderson, et al., J. Chem. Ecol., vol. 1, No. 4, pp. 493–499 (1975).

*Primary Examiner*—Donald G. Daus

*Assistant Examiner*—Diana G. Rivers

*Attorney, Agent, or Firm*—Richards, Harris & Medlock

[57] ABSTRACT

A kit for synthesizing a scent substantially similar to that produced in the anal glands of skunks is provided, consisting essentially of a first component comprising an aqueous solution of a trans-crotyl isothiuronium salt and a second component comprising an aqueous solution of base that, when combined, yield trans-2-butene-1-thiol.

A method for using the subject kit to mask human odor from detection by wild animals is also provided.

10 Claims, No Drawings

SYNTHESIZED SCENT

This is a division of application Ser. No. 885,941 filed Mar. 13, 1978, now U.S. Pat. No. 4,213,875.

BACKGROUND

This invention relates to synthesized scent substantially similar to that produced in the anal glands of skunks. The invention further relates to a kit for producing synthesized skunk scent, consisting essentially of a first component comprising an aqueous solution of a trans-crotyl isothiuronium salt and a second component comprising an aqueous solution of base that, when combined, yield trans-2-butene-1-thiol. The invention further relates to a method for masking human odor from detection by wild animals by use of the subject kit.

Hunters, trappers, photographers, and other persons having the need or desire to observe wild animals in their natural environment without detection have long sought methods of effectively masking their human odor. Many substances and preparations, both naturally occurring and synthetic, have therefore been marketed for the purpose of masking human odor from detection by wild animals. Many of these products attempt to mask the human odor with another, more predominant scent or odor that wild animals normally encounter in their natural environment and are therefore not suspicious of. A particularly effective scent for masking human odor from detection by wild animals is that produced in the anal gland of skunks.

The effectiveness of skunk scent at masking human odors has long been recognized. In spite of this, however, several obvious disadvantages associated with the collection, handling, storage and deployment of natural skunk scent have severely limited its availability for widespread use. Because of these disadvantages, many attempts have been made to produce a synthetic skunk scent so similar to the natural product that it will effectively mask the human odor without otherwise alarming wild animals in the vicinity where it is deployed.

In 1896, T. B. Aldrich published a study in the *Journal of Experimental Medicine* entitled "A chemical study of the secretion of the anal glands of *Mephitis mephitica* (common skunk), with remarks on the physiological properties of this secretion." In that paper, Aldrich claimed that the major constituent of skunk scent is 1-butanethiol. Until 1975, the analysis done by Aldrich was generally accepted and synthetic scents comprising 1-butanethiol were tested in the field. However, this testing disclosed that wild animals did not respond to the 1-butanethiol preparations in the same manner that they responded to natural skunk scent. Because of this, there still existed a need for a synthetic skunk scent indistinguishable by wild animals from the natural scent.

In 1975, K. K. Anderson and D. T. Burnstein published a paper entitled "Some Chemical Constituents of the Scent of the Striped Skunk." *J. Chem. Ecol.*, 1975, Vol. 1, No. 4, pp. 493–499. In that paper, Anderson and Burnstein identified a compound in skunk scent to be trans-2-butene-1-thiol. Two different methods for synthesizing trans-2-butene-1-thiol are disclosed in the literature. One method, disclosed in a paper by S. F. Birch and D. T. McAllan, *J. Chem. Soc.*, 1951: 2256–2563, involves the sodium-ammonia reduction of thiopene. The other method, also used by Birch and McAllan, and further disclosed in a paper by D. F. Lee, B. Saville and B. R. Trego, *Chem. & Ind.* (London), 1960: 868–869, involves the reaction of trans-crotyl isothiuronium bromide with sodium hydroxide to produce the trans-2-butene-1-thiol.

Also found by Anderson and Burnstein were minor amounts of two other compounds, 3-methyl-1-butanethiol and trans-2-butenyl methyl disulfide. The three compounds identified as the constituents of skunk scent by Anderson and Burnstein are themselves malodorous, and present many of the same problems encountered in handling, storing and deploying natural skunk scent.

A synthetic scent is therefore needed that is capable of masking human odor, yet is indistinguishable by wild animals from that which is naturally produced in the anal glands of skunks. The desired scent should not be malodorous during manufacture, storage or handling, but should be capable of being readily activated when deployed in the field. Furthermore, the scent should be volatile enough to disperse rapidly in the vicinity of the user, yet capable of prolonged masking protection.

SUMMARY OF THE INVENTION

According to the present invention, a kit is provided for synthesizing a scent substantially similar to that produced in the anal glands of skunks. The subject kit consists essentially of a first component comprising an aqueous solution of a trans-crotyl isothiuronium salt and a second component comprising an aqueous solution of base. When combined, the two components yield trans-2-butene-1-thiol, the predominant constituent of natural skunk scent.

A method for using the kit of the subject invention to mask human odor from detection by wild animals is also provided.

The invention disclosed herein will, for the first time, provide hunters, trappers, photographers, and the like with a synthetic scent substantially similar to the natural scent of skunks. The components of the subject kit are not malodorous during manufacture, storage or transporation, yet can be easily activated in the field. Furthermore, the scent produced according to the method of the invention disperses rapidly in air but is still capable of prolonged odor production when deployed in small quantities.

DETAILED DESCRIPTION OF THE INVENTION

The kit of this invention consists essentially of two components that can be easily combined in the field to produce trans-2-butene-1-thiol, the predominant constituent of natural skunk scent. The two essential components are aqueous solutions that are not malodorous so long as they are maintained apart from each other. The first component of the subject kit comprises an aqueous solution of a trans-crotyl isothiuronium salt. The preferred salt for use with the present invention is trans-crotyl isothiuronium chloride, a compound having the following molecular structure:

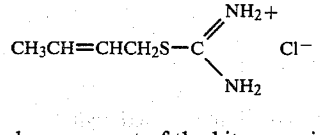

(I)

The second component of the kit comprises an aqueous solution of base, preferably selected from sodium hydroxide, sodium carbonate and mixtures thereof. When the two components are combined according to the method of the invention, they react to yield trans-2-butene-1-thiol.

Trans-crotyl isothiuronium chloride, the preferred salt for use with the invention, is believed to be a novel compound not previously disclosed in the literature. There is, however, evidence of trans-crotyl isothiuronium bromide, the bromine analog of the chloride salt, in the publications by Birch and McAllan, and Lee, Saville and Trego, referred to above. While the bromine analog can be utilized as the trans-crotyl isothiuronium salt of the invention, it is less desirable than the chloride salt. This is true partially because trans-crotyl bromide, from which trans-crotyl isothiuronium bromide is made, has a more pronounced lachrymal property than trans-crotyl chloride, the corresponding chlorine compound. Furthermore, the chloride salt is less expensive than the bromide salt, yet is adequately reactive for the present use.

The trans-crotyl isothiuronium chloride salt preferred for use in the first component of the kit of the invention is prepared by reacting trans-crotyl chloride with thiourea. Trans-crotyl chloride is a commercially available compound made by reacting hydrogen chloride with 1,3-butadiene. The form the trans-crotyl isothiuronium chloride salt, thiourea is first suspended in an inert solvent such as ethanol, isopropanol, normal butanol, isobutanol, and the like, or any other alcohol that remains inert at a reaction temperature ranging from about 40 to about 85 degrees C. A solvent comprising 95% ethanol has proven satisfactory for this purpose. The slurry of thiourea in alcohol should then be heated to a temperature almost equal to the boiling point of the solvent. Where the solvent is ethanol, a satisfactory temperature is about 80 degrees C.; where the solvent is isopropanol, a satisfactory temperature is about 85 degrees C. Once the slurry has been heated, an equimolar amount of trans-crotyl chloride is added thereto at a rate that is slow enough to keep the reaction under control. Because the reaction is very exothermic, adding all the trans-crotyl chloride at once can be dangerous. Next, the mixture is refluxed for approximately one hour at a temperature ranging from about 40 to about 85 degrees C., and preferably from about 60 to about 80 degrees C. It will be understood that the maximum reaction temperature is largely determined by the boiling point of the crotyl chloride, and that higher reaction temperatures can be used provided there is adequate means for withdrawing the heat of reaction. The alcohol solvent is then drawn off under a vacuum to yield the trans-crotyl isothiuronium chloride. Provided there is sufficient inert solvent to suspend the thiourea, the amount of solvent utilized is not critical. However, it should be noted that excess solvent slows the reaction, requiring more refluxing to achieve the same yield.

To prepare the first component of the subject kit, the trans-crotyl isothiuronium salt thus obtained is dissolved in water. A half molar concentration of trans-crotyl isothiuronium chloride in water has proven particularly effective for use in the present invention.

The second component of the subject kit comprises an aqueous solution of base, preferably selected from sodium hydroxide, sodium carbonate, and mixtures thereof. In the above-mentioned paper by Birch and McAllen, the isothiuronium bromide salt was reacted with sodium hydroxide to produce the crotyl mercaptan. I have found aqueous solutions of sodium hydroxide and sodium carbonate to be similarly effective for producing trans-2-butene-1-thiol when reacted with an aqueous solution of trans-crotyl isothiuronium chloride. I have also discovered, however, that unexpected and superior results can be achieved by utilizing as the second component of the subject kit an aqueous solution having a half molar concentration of sodium hydroxide in addition to a half molar concentration of sodium carbonate. While the reasons for this improved reaction are not entirely clear, it is believed to result from the buffering effect of the carbonate on the more basic sodium hydroxide.

When an aqueous mixture of sodium hydroxide and sodium carbonate is utilized as the second component of the kit, the trans-2-butene-1-thiol is produced more rapidly than when sodium carbonate is used by itself. When sodium hydroxide is used alone, the trans-2-butene-1-thiol is produced very rapidly, but because of the excess of strong base present, the thiol is immediately converted in some degree at least to its less volatile sodium salt. Mercaptans are more acidic than alcohols, and will dissolve in aqueous sodium hydroxide to form water-soluble sodium salts, which would not be volatile. Probably at the lower pH produced by the mixture of sodium hydroxide and sodium carbonate, the pH is high enough to permit the rapid formation of trans-2-butene-1-thiol, but not high enough to tie up much of the mercaptan in the non-volatile form. And, for this reason, the desired odor is not produced as quickly and to the same degree when sodium hydroxide is used alone, as when the mixture of sodium hydroxide with sodium carbonate is used.

Although sodium hydroxide, sodium carbonate, and mixtures thereof are preferred bases for use with the present invention, other bases can also be used. For example, potassium hydroxide or lithium hydroxide can be substituted for sodium hydroxide, and potassium carbonate can be substituted for sodium carbonate.

While the first and second components described above are considered to be essential to the present invention, other components can also be included for improving the effectiveness of the synthetic scent and increasing its similarity to scent naturally produced by skunks. As mentioned above, Anderson and Burnstein found some 3-methyl-1-butanethiol present with the trans-2-butene-1- thiol in the natural scent. Although I have not found it necessary to incorporate the 3-methyl-1-butanethiol in order to achieve satisfactory results with my invention, the method disclosed above for preparing the components required for producing trans-2-butene-1-thiol are similarly applicable to this compound. The reaction of 3-methyl-1-chlorobutane, 3-methyl-1-bromobutane, or 3-methyl-1-iodobutane with thiourea yields the associated isothiuronium salt that can be reacted with the aqueous solution of base as previously disclosed to yield 3-methyl-1-butanethiol. Where it is desired to include this compound in the kit of the subject invention, a minor effective amount of the isothiuronium salt thus produced can be added to the aqueous solution already disclosed as the first component of the subject kit. In that event, it is also desirable to increase the total concentration of base in the second component by an equal amount.

The addition of a humectant to the kit has also proven useful for reducing the evaporation rate of the combined components when deployed in the field, thus prolonging the odor production. Humectants suitable for use in the invention include glycerol, glycols, sorbitols, and mixtures thereof. According to a preferred embodiment of the invention, 10% by volume of glycerol is included in at least one component of the kit.

If desired, inert coloring agents can also be added to either or both components of the kit. The preferred inert coloring agent for use with the invention is dichloro-fluorescein, a yellowish, fluorescent compound that is stable in the basic solution of the second component and resists fading.

The component solutions can be easily packaged by conventional means such as, for example, small plastic squeeze bottles containing from about one to about four ounces of solution and capable of dispensing the solution drop by drop. While other packaging means can also be used within the scope of the invention, large quantities of solutions are generally not required and safisfactory results are achieved in most applications by using about twenty drops of each solution. According to a preferred embodiment of the invention, the bottles containing the two component solutions comprising the subject kit are packaged together in a suitable outer wrapper or container such as, for example, a cardboard box. A sheet of printed instructions is also included in the package, directing the user in the method of the invention.

According to the method of the invention, a scent substantially similar to that produced in the anal glands of skunks is made by providing a first component comprising an aqueous solution of a trans-crotyl isothiuronium salt, providing a second component comprising an aqueous solution of base, and thereafter contacting the two components, producing trans-2-butene-1-thiol. In a preferred manner for practicing the method of the invention so as to mask human odor from detection by wild animals, about twenty drops of the first component are contacted with about twenty drops of the second component at each of two or more locations in the vicinity of the person whose odor is sought to be masked. Because human odor is carried by the wind and is normally detected by wild animals on the downwind side, it is desirable to deploy the subject scent downwind of the user and between the user and said animals. The scent is preferably deployed by contacting the subject components on each of two absorbant surfaces positioned downwind of the user in such manner that the angle formed between the position points, with the user at the vertex, is about 45 degrees. The distance from the user to the position points will vary according to wind conditions, but can vary from about 10 to about 25 yards, or more. Deployment of the scent in more than one location will promote dispersion of the trans-2-butene-1-thiol throughout the air in the vicinity surrounding the user, and will therefore provide better masking protection. Furthermore, by combining the two components on a cloth, stick, or the like, it is possible to reposition the odor sources in the event that the wind direction changes.

As will be apparent to those of ordinary skill in the art upon reading the present disclosure, other variations, alterations, substitutions and equivalents may be applicable to the various embodiments disclosed herein. It is the intent, however, that the concepts disclosed herein be limited only by the appended claims.

What I claim is:

1. A method for synthesizing a scent substantially similar to that produced in the anal glands of skunks and useful to prevent wild animals from detecting the presence of a user in their natural environments, comprising the steps of:

(a) providing a first component comprising an aqueous solution of a trans-crotyl isothiuronium salt;

(b) providing a second component comprising an aqueous solution of a first base selected from the group consisting of sodium hydroxide, potassium hydroxide and lithium hydroxide and a second base selected from the group consisting of sodium carbonate and potassium carbonate, said second base present in an effective amount for increasing the degree and rate of production of the scent when said first component is mixed with said second component; and (c) contacting said first component with said second component, thereby producing trans-2-butene-1-thiol.

2. The method of claim 1 wherein the trans-crotyl isothiuronium salt is selected from the group consisting of trans-crotyl isothiuronium bromide and trans-crotyl isothiuronium chloride.

3. The method of claim 1 wherein the trans-crotyl isothiuronium salt is present in about a half molar concentration.

4. The method of claim 1 wherein said second component comprises an aqueous solution comprising about a half molar concentration of sodium hydroxide and about a half molar concentration of sodium carbonate.

5. The method of claim 1 wherein at least one of said components further comprises a humectant.

6. The method of claim 5 wherein the humectant is selected from the group consisting of glycerol, glycols, sorbitols, and mixtures thereof.

7. The method of claim 1 wherein at least one of said components further comprises about 10% by volume of a humectant.

8. The method of claim 1 wherein at least one of said components further comprises a minor effective amount of a coloring agent.

9. The method of claim 8 wherein the coloring agent is dichloro-fluorescein.

10. The method of claim 1 wherein said first component further comprises another type of isothiuronium salt, produced by the reaction of a compound selected from the group consisting of 3-methyl-1-chlorobutane, 3-methyl-1-bromobutane and 3-methyl-1-iodobutane with thiourea, for producing 3-methyl-1-butanethiol when said isothiuronium salt is mixed with said second component.

* * * * *